(12) United States Patent
Carroll et al.

(10) Patent No.: US 6,572,567 B1
(45) Date of Patent: Jun. 3, 2003

(54) MOBILE LIFT SYSTEM AND METHOD OF USE

(75) Inventors: Michael Carroll, Taylorsville, UT (US); Benjamin Vance, Sandy, UT (US)

(73) Assignee: Zevex, Inc., Salt Lake City, UT (US)

( * ) Notice: Subject to any disclaimer, the term of this patent is extended or adjusted under 35 U.S.C. 154(b) by 38 days.

(21) Appl. No.: 09/967,472

(22) Filed: Sep. 28, 2001

(51) Int. Cl.[7] .......................... A61B 5/103; A61B 5/117
(52) U.S. Cl. ........................................... 600/587
(58) Field of Search ........................ 600/587, 483, 600/502, 520; 73/862.03, 862.042, 379.01, 379.02, 379.08; 273/440, 451; 482/92, 91, 121, 131, 6

(56) References Cited

U.S. PATENT DOCUMENTS 5,275,045 A * 1/1994 Johnston et al. ......... 73/379.01
5,348,519 A * 9/1994 Prince et al. ................... 482/6
5,435,315 A * 7/1995 McPhee et al. ............. 600/483
6,227,047 B1 * 5/2001 Livingston ............... 73/379.08

OTHER PUBLICATIONS

Jackson Strength Evaluation System, http://www.rehaboutlet.com, pp. 1–4.*

* cited by examiner

Primary Examiner—Max F. Hindenburg
Assistant Examiner—Brian Szmal
(74) Attorney, Agent, or Firm—Morriss, Bateman, O'Bryant & Compagni

(57) ABSTRACT

A mobile lift system includes a platform configured for receiving a patient, an attachment rail which extends from the platform, and an attachment member for holding a belt to the attachment rail, and for selectively moving to point along the rail at which the belt is attached. The attachment rail can be removably attached to the platform, or may be pivotable with respect to the platform to facilitate storage and transport of the mobile lift system.

34 Claims, 5 Drawing Sheets

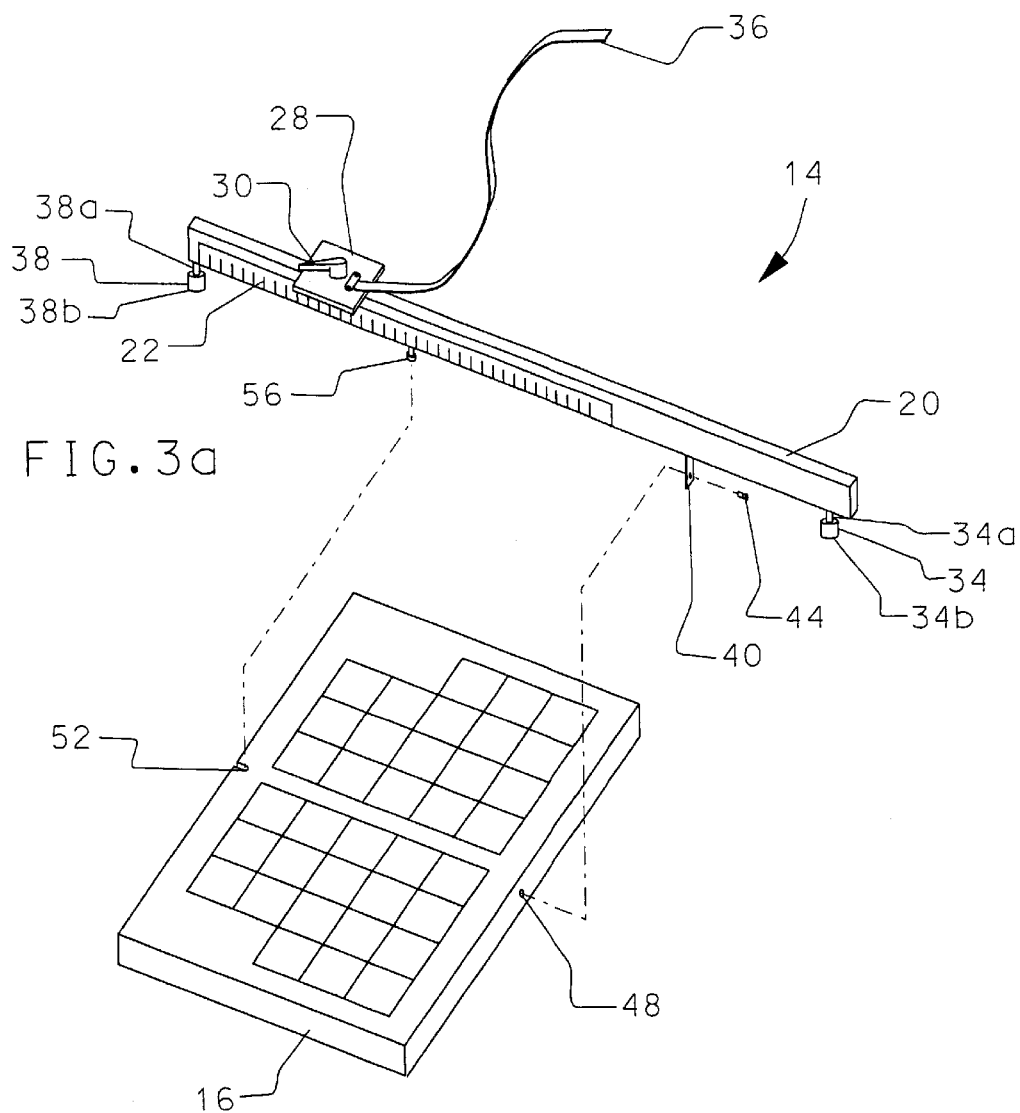
FIG.3a
FIG.3b
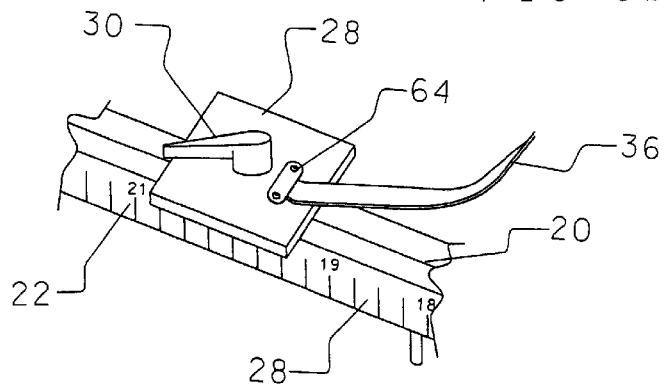
FIG.4

MOBILE LIFT SYSTEM AND METHOD OF USE

BACKGROUND OF THE INVENTION

1. The Field of the Invention

The present invention relates to an apparatus used in conducting isometric testing of individual muscles, muscle groups or joints in physical and occupational therapy diagnosis, and individual functional capacity assessment in employment evaluations. More specifically, the present invention relates to an improved device used in conducting static lift tests, which improves the range of tests which can be performed and which also improves the portability of the device.

2. State of the Art

Isometric assessment of muscular strength typically involves a maximum voluntary contraction at specific joint angles or functional positions against an unyielding platform or handle connected to a device that measures force. Isometric techniques have been employed extensively in orthopedic, sports, rehabilitation, occupational, and industrial clinics for over four decades. Prior to the vast availability of isometric testing products, muscular strength was clinically assessed by methods of isokinetic testing. Isokinetic testing measures strength throughout a range of motion of a body using a yielding, constant velocity device in connection with a force measuring device. This method of testing has become increasingly less common due to the presence of isometric testing products.

The first of such isometric testing devices were developed in the early 1980s and involved measurement of the maximal force using a cable tension meter or dial gauge. Characteristically, these devices are typically composed of a platform upon which the patient stands while pulling upward on a cable connected to the platform. These types of isometric tests are known as "lift tests," and are limited to the assessment of large gross forces at only a limited number of muscle groups.

Isometric lift tests provide valuable information to therapists about the functional capacity of an individual's strength at large muscle groups and joints. These tests also provide occupational therapists and employers with insight regarding the extent of an employee's ability to functional in various capacities in the workplace.

Though more advanced isometric testing products have been developed in recent years that are more effectively adapted to allow customized isometric testing of particular muscle groups, the basic model allowing only simple lift tests are still widely used. Such products are relatively easy to use and are relatively inexpensive. However, several disadvantages have been recognized in the basic lift test models.

One disadvantage of the basic lift test model is the weight of the apparatus, which is heavy and difficult to move. The large platform constituting the major weight of the apparatus is thick and heavy so that the patient being tested may exert maximum contraction without the platform to which the cable is attached yielding to the force. The size of the platform was also used to eliminate the risk of mechanical leverage caused by the patient's exertion from lifting the front of the platform and tipping it backward—potentially causing the patient to fall. The weight and size of the platform, however, make it difficult for occupational therapists and the like to take the isometric testing device to patients at remote locations. However, smaller and lighter platforms have generally been avoided because of the risk of the platform tipping.

Nevertheless, it is found that the platform need not be so heavy because the nature of a lift test is such that the weight of the individual typically is centered over the point of opposite force exerted by the same individual, preventing the platform from yielding to the opposite force. Thus, the device need not be heavy, large, or difficult to transport. In light of the problems with the prior art, however, there is a need for a device that weighs less and is more easily moved and transported, while still offering sufficient resistance to the opposing force of the patient's contraction and minimizing mechanical leverage if the patient leans back during the test. Such a device should be more easily transported to on-site evaluations, and could be easily moved or adjusted during actual testing.

Another disadvantage of the basic lift model is the surface area of the apparatus and the consequent space required for its storage. The platform of existing models is typically 30"×48", and occupies a significant portion of a typical office floor. The size of the platform occupies a large portion of a closet, and rarely fits into smaller storage spaces. The bulky nature of the platform makes it difficult to store away. This is particularly important for physical therapists and occupational therapists who travel to their patients or to various clinics to conduct testing or treatment. The large platform will not fit in many automobile trunks. Thus, there is a need for a basic lift model that can be conveniently stored away in smaller spaces. There is also a need for an apparatus that occupies less floor space while either being used, stored in the open, or transported.

A further disadvantage of the basic lift model is the inability to accommodate specialized lifts designated by the physician. The prior art contains a single stationary attachment on the platform for the belt to which the opposing force is applied, which limits the range of variation of muscle groups that can be tested while the patient stands in a single position. In other words, for a patient to perform several of the NIOSH standardized lift tests, he must vary his position on the platform to create the appropriate angles and positions. Varying the patient's position on the platform to conduct multiple NIOSH tests makes repeat testing of the identical test difficult.

Thus, there is a need for the platform to contain an adjustment mechanism that can allow the belt to be positioned along an axis of the platform to accommodate specialized lift tests designated by the physician and that can more easily accommodate repeat testing without changing the position of the patient. A sliding mechanism would allow the patient to remain stationary while the physical therapist or occupation therapist slides the point of the belt attachment along the rail to create a new angle of force exertion. The new angles allow testing of different muscle and joint groups, or to find particular weaknesses long the patient's range of motion for a particular joint. Of course, other adjustment mechanisms which do not slide could also be used.

In view of the above mentioned disadvantages of the existing devices, it would be an advance in the industry of isometric lift testing devices to provide an apparatus for isometric lift tests, which is easily transportable, relatively light and over comes other disadvantages of the prior art.

SUMMARY OF THE INVENTION

It is an object of the present invention to provide a mobile lift system and method of use that improves upon the existing technology of isometric lift test devices.

The above and other objects and advantages of the present invention are accomplished by a mobile lift system having a platform which is generally smaller than the platforms of the prior art lift systems, and an attachment rail that engages the platform.

The platform of the mobile lift system is preferably smaller than the platforms of prior art lift systems, and the attachment rail extends from the platform to enable a point of attachment for the cable used for the isometric test to be positioned away from the platform. The rail may be adjusted relative to or removed from the platform when not in use to reduce the overall dimensions of the mobile lift system. This, in turn, requires less space for storage and allows easier transportation of the apparatus to on-site testing locations.

In accordance with one aspect of the present invention at least bracing member is disposed along the attachment rail. The bracing member is positioned to prevent the patient from lifting the front end of the platform by leaning rearwardly while performing a lift. Preferably, the bracing member will extend down into contact with the surface on which the platform is placed. However, the bracing member could be disposed slightly above that surface so that it only engages the surface one the mechanical leverage caused by the patient is about to cause the front end of the platform to be lifted off the ground.

In accordance with another aspect of the present invention, the mobile lift system includes an attachment member which is adjustable so that it may be positioned at various locations along the attachment rail. The attachment member allows the lower end of a belt or cable used for isometric testing to be moved between a variety of positions along the attachment rail. By simply adjusting the attachment member along the attachment rail, the therapist can test a wide range of lift positions while the patient remains in the same position. These accommodations of the present invention also allow the therapist to perform various tests without moving the position of the patient, which will accommodate accurate repeat tests of the patient in the same position.

In accordance with yet another aspect of the present invention, the attachment rail is ruled and the attachment member is provided with a quick release mechanism that makes adjusting the attachment member along the attachment rail simple and easy. The configuration of the attachment member also locks securely along the attachment rail to ensure safe lift tests. Additionally, by marking the position of the patient on the platform and the location of the slide block assembly along the ruled attachment rail, the therapist can readily repeat tests over a period of time to monitor a patient's improvement.

BRIEF DESCRIPTION OF THE DRAWINGS

The above and other objects, features and drawings of the invention will become apparent from consideration of the following detailed description presented in connection with the accompanying drawings in which:

FIG. 3 shows a partially exploded perspective view of the mobile lift system of FIG. 2;

FIG. 4 shows a close-up view of the attachment rail and attachment member shown in FIGS. 2 and 3 with the attachment rail and attachment member detached from the platform;

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Referring again to FIG. 1, there is shown a lift system made in accordance with the teachings of the prior art. The lift system of the prior art includes a platform 4 upon which a patient stands in order to test isometric strength of various muscle groups. The platform 4 is typically about 30 inches wide and 48 inches long. The platform 4 is of such a size in order to accommodate the patient in different positions along the platform in order to test various muscle and joint groups. A cable or belt attachment 8 on the prior art platform 4 is fixed in a single position, centered relative to the width and forward on the platform. Lines 12 running the width of the platform constitute a guide on the platform for the patient's feet relative to the fixed position of the belt attachment 8.

Figure 1:
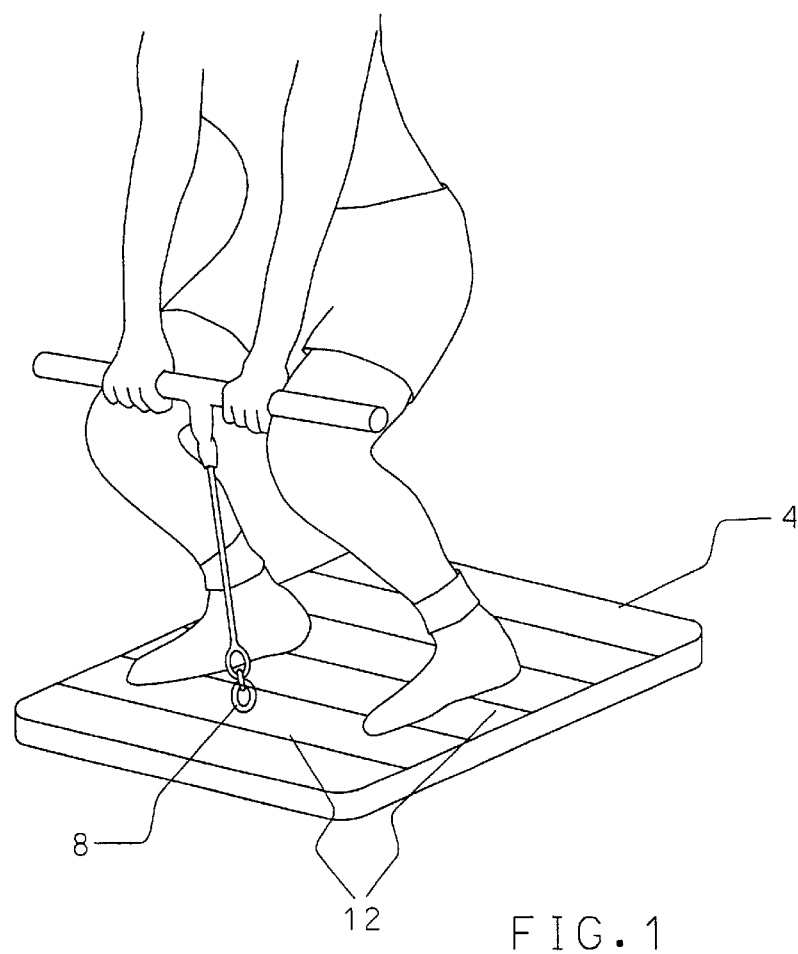
FIG. 1 shows a side view of an individual performing a static lift test on the prior art.

The configuration of the prior art embodiment shown in FIG. 1 makes repeat testing of particular angles of lift somewhat difficult because the fixed position of the belt attachment 8 mandates that the patient move towards the belt attachment or away from it on the platform 4 to properly align for proper testing. Thus, if a therapist were to test a patient in a particular position, and then change the position of the patient upon the platform 4 returning to the original position would be less than exact, and may result in a skewed measurement of muscle strength or joint flexion. This is especially so where the measurements of various muscle groups or joints are taken over a prolonged period of time to monitor whether a patient is progressing, and where the patient's position is not in exact alignment with the lines 12 on the top of the platform 4.

In addition to the above, the platform 4 is relatively large and can be difficult to place in a automobile trunk and the like. Those skilled in the art will appreciate that while a small platform could be used, such a platform would significantly limit the positions of the patient on the platform, thereby limiting the different tests which can be performed with the platform.

Figure 2:
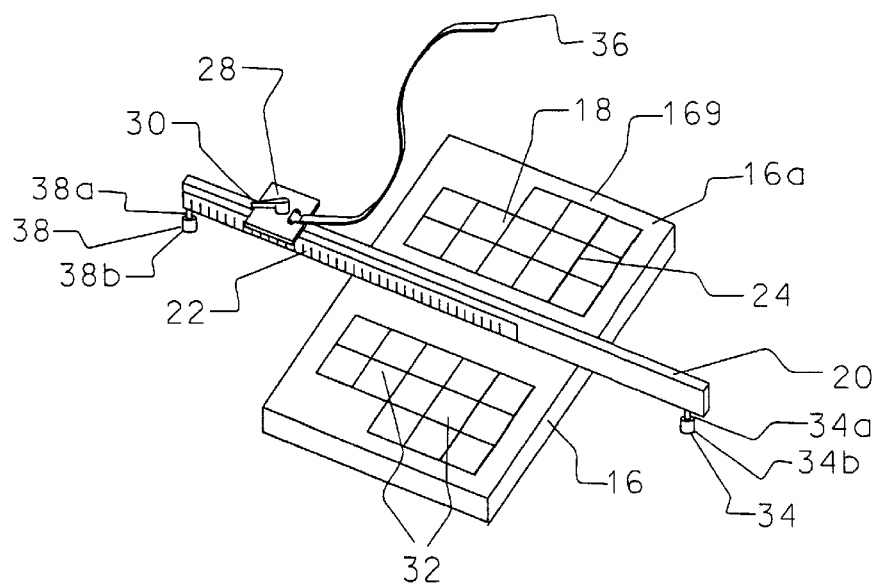
FIG. 2 shows a perspective view of a mobile lift system made in accordance with the principles of the present invention.

Turning now to FIG. 2, there is shown a top view of a mobile lift system, generally indicated at 14, made in accordance with the principles of the present invention. The mobile lift system 14 includes a platform 16 which is generally smaller than the platform 4 (FIG. 1) of the prior art. Disposed on the upper surface 16a of the platform 16 is a series of lines forming a grid 18.

An attachment rail 20 extends along the platform 16. The attachment rail 20 preferably bisects the upper surface 16a of the platform 16 so that the patient can conveniently place one foot on each side of the attachment rail. It should be understood, however, that the attachment rail 20 need not bisect the platform 16. Those skilled in the art will appreciate that the attachment rail 20 could be placed off center if desired. Additionally, the attachment rail 20 could simply extend from the platform 16.

The attachment rail 20 is typically between 23 inches and 42 inches long, although longer lengths and shorter lengths can be used. Most preferably the attachment rail 20 is 42 inches long, while the platform 16 is 30 inches wide and 15 inches deep. Thus, the attachment rail 20 extends between about 16–17 inches beyond the front end of the platform 16, and about 10–11 inches beyond the back end of the platform when a 42 inch attachment rail is used, and about 4 inches in front and 4 inches behind when a 23 inch attachment rail is used.

The attachment rail 20 has a plurality of markings 22 disposed thereon. While the markings are typically units of measurement, such as inches or centimeters, other markings can be used to record location along the attachment rail 20.

As shown in FIG. 2, the markings 22 along the attachment rail 20 begin from a base line 24 on the grid. Thus, the base line is position 0 and the attachment bar 20 extends a distance, typically 24 inches therefrom. As will be explained momentarily, the user may stand with his or her medial malleolus over the base line and the point from which the lift test is conducted may be at any location from the base line 24 up to 24 inches forward. (Longer lengths can be achieved by using a longer attachment rail). If desired, the point of attachment for the test could even be behind the base line 24. Likewise, the base line could be positioned at the front of the user's feet, or at some other location.

Disposed along the attachment rail is a belt attachment member 28 to which a cable or belt 36 is attached. Unlike the prior art shown in FIG. 1 wherein the belt is attached to a static location along the platform, the attachment member 28 attaches the belt 36 at a number of locations along the attachment rail 20 to create any of a number of angles of pull, and accommodate various lift positions without the patient having to move on the platform 16.

The belt attachment member 28 is configured with an engagement mechanism 30 to engage the portion of the attachment rail 20 that is provided with the markings 22 to selectively hold the belt attachment block assembly at a given location along the attachment rail 20 while a lift is performed by the patient. Limiting movement of the belt attachment member 28 can be accomplished by rotation of a bolt, by insertion of a pin or any other mechanical or electrical mechanism for preventing movement of the belt attachment member. As shown in FIG. 2, the engagement mechanism is formed by a quick release lever 30 which utilizes a cam or other engagement mechanism to engage the attachment rail 20.

Also shown in FIG. 2 are a pair of bracing members 34 and 38 which are disposed adjacent opposing ends of the attachment rail 20. The bracing members 34 and 38 preferably engage the surface on which the platform 16 rests. The rear bracing member 34 is particularly beneficial in that it prevents a patient from accidentally lifting the forward end of the attachment rail 20 and the platform up by leaning backward while performing a lift. While the bracing members can be formed from a variety of components, they typically include a post 34a and 38a which engages the attachment rail, and a soft, non-marking material, such as rubber or foam which will prevent damage to the surface in the event that the patient lean backward and the bracing member must stop the mechanical leverage by engaging the flooring surface.

In use, the patient stands on the platform 16 at a set location, typically with his or her medial malleolus over the base line 24. If the belt attachment member 28 is not already in the desired position for the patient's first lift, the therapist loosens the engagement mechanism 30 and moves the belt attachment member 28 into the desired position. (It will be appreciated by those skilled in the art that the belt attachment member 28 may be moved by other than sliding. However, having the belt attachment member 28 slide along the attachment rail 20 decreases the likelihood that the attachment member will fall off the attachment rail and get lost as the mobile lift system is moved between locations or stored.)

Once the patient has completed the first lift test, the therapist can then move the belt attachment member 28 into a second position for conducting further tests without requiring any movement of the patient. While the therapist may record the position of the belt attachment member 28 during each test, the therapist may also come to associate certain positions with a certain test regardless of the size of the patient. Regardless of whether the location of the belt attachment member 28 is recorded or simply remembered by the therapist, the patient can engage in numerous repeatable tests without having to move on the platform 16. However, marking the positions of the belt attachment member 28 along the attachment rail 20 enables the therapist to move the patient to new lift positions and angles and then to easily return to the previous lift positions and angles. It also allows for more accurate recording so that trends in the patient's progress can be monitored.

Turning now to FIG. 3, there is shown an exploded or disassembled view of the mobile lift system 14 showing the individual components which form the mobile lift system. The attachment rail 20 connects to and separates from the platform 16 to facilitate transfer and storage of the mobile lift system 14 when not in use.

The attachment rail 20 attaches to the platform 16 by an attachment means, such as placing an anchor pin 44 through a lock pin bracket 40, located on the attachment rail 20, and into a receptacle 48 in the platform 16. An attachment post 56 also extends from the attachment rail 20 and slides into engagement with an attachment post notch 52 in the platform to form an attachment means. Typically, the attachment post 56 is slid into the attachment post notch 52, the lock pin bracket 40 is slid into alignment with the receptacle 48, and the anchor pin 44 inserted.

To remove the attachment rail 20 from the platform 16, the anchor pin 44 is removed from the lock pin bracket 40 and the attachment post 56 is slid out of the attachment post notch 52. The attachment rail 20 can then be pulled away from the platform 16 and stored together or separately.

The belt attachment member 28, show in close-up in FIG. 4, attaches to the attachment rail 20 and slides thereon. As mentioned above, the sliding of the belt attachment member is preferred, but not required. Having the belt attachment member 28 slide allows for easy movement while minimizing the risk that the belt attachment member will get lost.

To release the belt attachment member 28 in order to move it to a new position along the attachment rail 20, the lever 30 is turned counterclockwise. The belt attachment member 28 is then released and freely moves along the attachment rail 20. The exact position of the belt attachment member 28 along the attachment rail 20 is indicated by the markings 22 on the attachment rail.

The belt attachment member 28 can then be fastened to a fixed position along the attachment rail 20 by turning the lever 30 in a clockwise position. A cam (not shown) attached to the lever 30 engages the attachment rail 20 to prevent movement of the belt attachment member 28.

When the belt attachment member 28 is fastened in this manner to the attachment rail 20, the patient may then safely conduct a lift test by pulling on the belt 36. The occupational therapist or physical therapist conducting the test can record the force exerted, and then can move the attachment member 28 to another position along the attachment rail 20 for another test. If desired, the therapist can return the belt attachment member 28 to the original position to redo the initial test without moving the patient. Such may be used, for example, if attempting to determine the differences between the patient's lifting capacity initially, and after strenuous exertion.

Also shown in FIG. 4 are a pair of screws 64 which are used to anchor the belt 36 to the belt attachment member 28. Those skilled in the art will appreciate that, as used herein, belt 36 is meant to include traditional belts, as wells as ropes, cords, cables, bands and similar devices, and the belt attachment member 28 to include structures for attaching the same.

Figure 5:
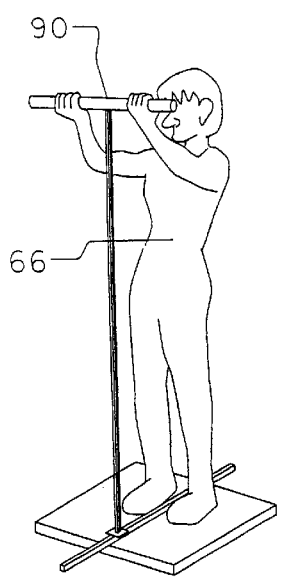
FIG. 5 shows a perspective view of an individual performing a high/far arm lift.
Figure 5A:
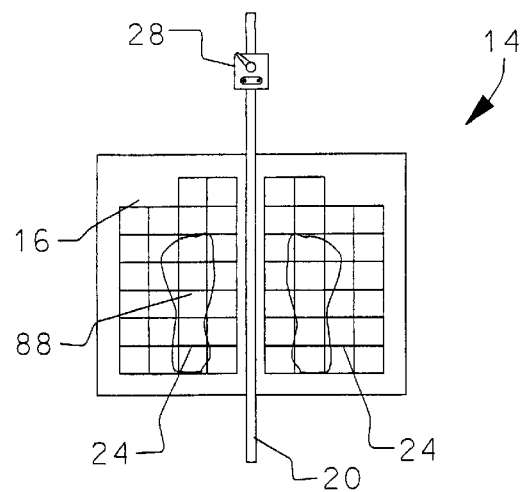
FIG. 5A shows a top view of the mobile lift system with indicia indicating the location of the patient's feet and the position of the attachment member when performing the high/far arm lift shown in FIG. 5.

Turning now to FIGS. 5 and 5A, there is shown a perspective view of a patient 66 performing an high/far arm lift, and a top view of the mobile lift system 14, indicating the location of the patient's feet 88 on the platform 16 for the test.

The patient 66 stands with his feet 88 positioned so that the medial malleolus are above the base line 24 on the platform 16. The belt attachment member 28 is moved into the desired position along the attachment rail 20. As shown in FIG. 5A, the attachment member 28 is typically about 20 inches from the base line 24 for the test. As the patient 66 pulls upwardly on a bar 90, the therapist is able to read a gage or other strain measuring device (not shown) to determine the force which the patient can apply. (Strain gages are commonly used in the art and are therefore not discussed in detail). While the therapist can use a single reading to determine the ability of the patient 66 at that point in time, the measurement can also be used in conjunction with other measurements for the same test over a period of time to monitor the patient's progress. Of course, the accuracy of the progress calculation is dependent on obtaining consistent data.

Figure 6:
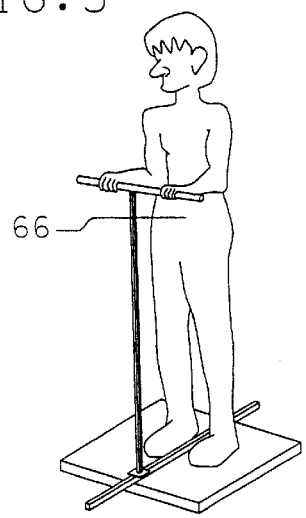
FIG. 6 shows a perspective view of an individual performing an arm curl.
Figure 6A:
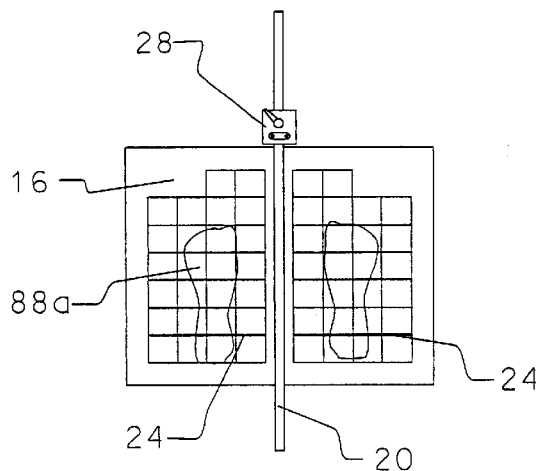
FIG. 6A shows a top view of the mobile lift system with indicia indicating the location of the patient's feet and the position of the attachment member when performing the arm curl shown in FIG. 6.

Turning now to FIGS. 6 and 6A, there is shown, respectively, a patient 66 performing an arm lift, and a top view of the mobile lift system 14 and the location of the patient's feet 88a on the platform 16. Instead of being positioned about 22 inches from the base line 24, the attachment member 28 is positioned directly below the patient's hands with elbows held at 90 degrees. This provides a more appropriate position for conducting an arm lift. As with the high/far arm lift shown in FIG. 5, the patient's feet 88a can remain stationary between tests.

Figure 7:
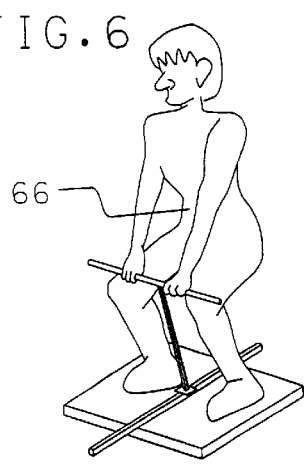
FIG. 7 shows a perspective view of an individual performing a squat lift.
Figure 7A:
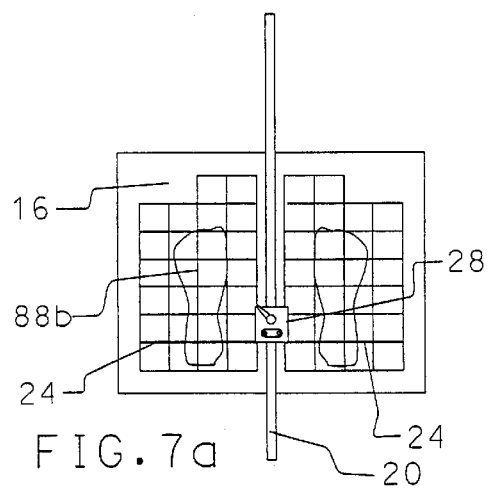
FIG. 7A shows a top view of the mobile lift system with indicia indicating the location of the patient's feet and the position of the attachment member when performing the high/far arm lift shown in FIG. 7.

FIGS. 7 and 7A show, respectively, a perspective view of a patient 66 performing a leg lift, and a top view of the mobile lift system 14 to demonstrate the location of the patient's feet 88b and the location of the attachment member 28 along the attachment rail 20.

Because of the muscle groups being tested, the attachment member 28 is typically moved to a location adjacent the base line 24, or a position adjacent the patient's ankles 88b. This allows the therapist to adequately test the strength of the quadriceps, as well as that of the knees. As with the previous positions, the patient's medial malleolus 88b are maintained above the base line 24.

Figure 8:
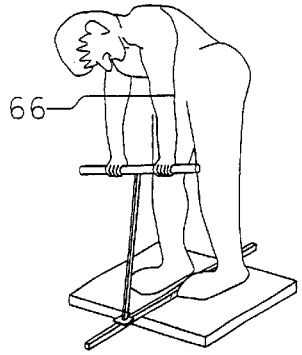
FIG. 8 shows a perspective view of an individual performing a mid-height torso lift.
Figure 8A:
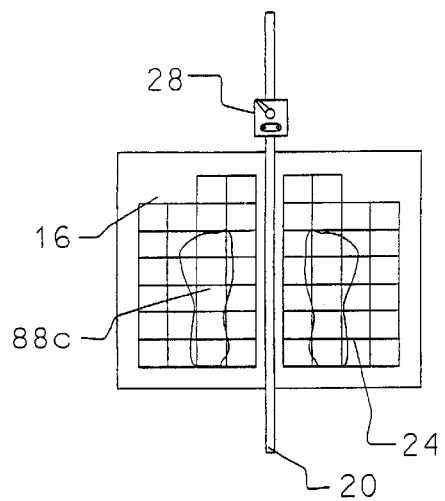
FIG. 8A shows a top view of the mobile lift system with indicia indicating the location of the patient's feet and the position of the attachment member when performing the mid-height torso lift shown in FIG. 8.

FIG. 8 shows a perspective view of a patient 66 performing a torso lift, while FIG. 8A shows the position of the patient's feet 88c on the platform 16 of the mobile lift system 14, as well as the position of the attachment member 28 along the attachment rail 20. Because the patient 66 is bending over during the lift, the attachment member 28 is positioned about 15 inches from the baseline 24 along the attachment rail 20.

Figure 9:
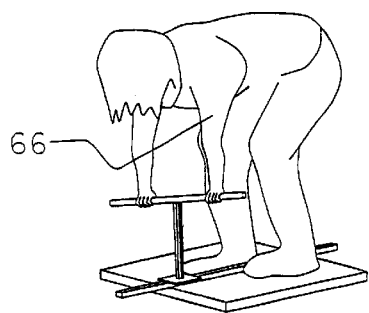
FIG. 9 shows a perspective view of an individual performing a low-height torso lift.
Figure 9A:
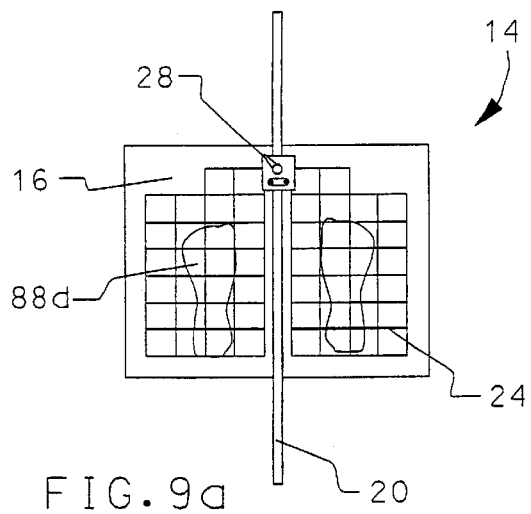
FIG. 9A shows a top view of the mobile lift system with indicia indicating the location of the patient's feet and the position of the attachment member when performing the low-height torso lift shown in FIG. 9.

FIG. 9 shows a perspective view of a patient 66 performing a floor lift. While the patient's feet 88d (FIG. 9A) are positioned adjacent the base line 24, the attachment member 28 is moved out to a position 10 inches from the base line. An alternate attachment adjacent to the attachment rail 20, approximately 10 inches away from the base line is provided to allow larger gauges to meet the 6 inch above the platform handle requirement of the tests. Thus, the therapist, etc., is able to test the ability of the patient to lift heavy objects off the floor in a controlled environment where injury to the back can be prevented.

Figure 10:
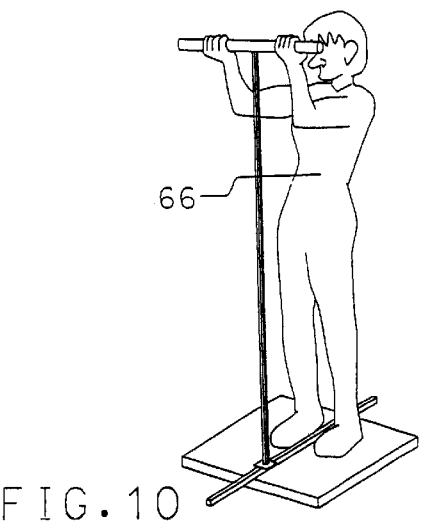
FIG. 10 shows a perspective view of an individual performing a high/near arm lift.
Figure 10A:
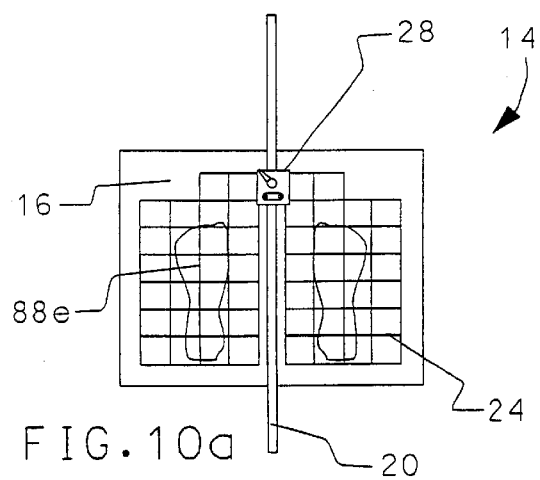
FIG. 10A shows a top view of the mobile lift system with indicia indicating the location of the patient's feet and the position of the attachment member when performing the high/near arm lift shown in FIG. 10.

FIG. 10 shows a perspective view of a patient 66 performing a high/near arm lift, while FIG. 10A shows a top view of the mobile lift system 14 indicating the location of the patient's feet 88e and the position of the attachment member 28 along the attachment rail 20. Because the bar 90 is being raised adjacent to the patient's face, the attachment member 28 is positioned about 10 inches in front of the base line 24, a short distance forward of the patient's feet 88e.

As will be appreciated from the forgoing, the therapist is able to conduct a number of tests without ever moving the patient. If desired, the therapist can repeatedly move between tests to monitor endurance, and whether strain on one muscle group is impacting the functioning of another muscle group.

Once the therapist is finished with the test, the anchor pin 44 need only be removed from the lock pin bracket 40 and the attachment post 56 slid out of the attachment post notch 52 for the platform 16 and the attachment rail 20 to be separated and either transported or stored. By at least partially disassembling the mobile lift system, it can be made to more easily transportable and can be stored in a smaller space. Of course, the attachment rail 20 and the platform 16 need not be fully disassembled to facilitate storage and/or transport.

Figure 11:
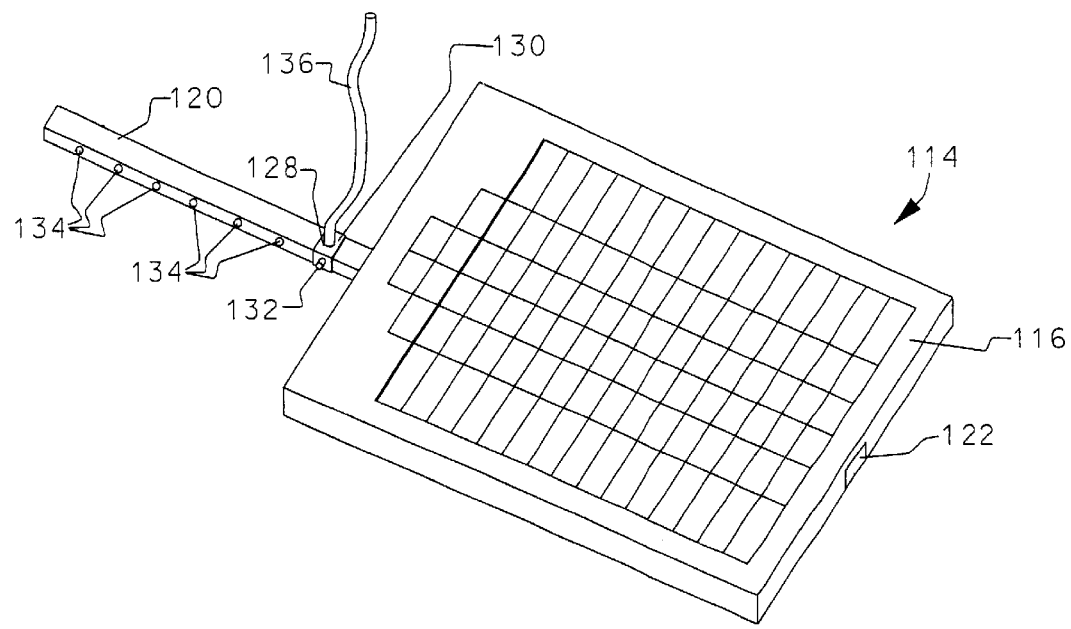
FIG. 11 shows a top perspective view of another embodiment of a mobile lift system in accordance with the principles of the present invention.

Turning now to FIG. 11, there is shown another embodiment of a mobile lift system 114 made in accordance with the principles of the present invention. The mobile lift system 114 includes a platform 116 and an attachment rail 120. Unlike the attachment rail 20 discussed above, the attachment rail 120 shown in FIG. 11 nests in a channel 122 in the platform 116. The attachment rail 122 can either be temporarily fixed with respect to the platform 116 by placement of a pin or some other retainer, or can be made to slide relative to the platform.

If the attachment rail 120 is temporarily fixed with respect to the platform 116, a mechanism is provided to attach an attachment member assembly 128 at various locations along the attachment rail 120. The attachment member 128 can be a block, a sleeve 130, a pin 132 or other mechanism for connecting the belt 136, cable, etc., to the attachment rail 120. Thus, as shown in FIG. 11, the attachment member 128 is a sleeve 130 which wraps around the attachment rail 120 and a pin 132 which is received in any of a number of holes 134 formed in the attachment rail.

In such a configuration, the attachment member 128 may be moved to accommodate different tests simply by moving the pin 130 to a hole 134 at the desired location. While a plurality of holes 124 provides less precision than a slidable attachment member 28 along a ruled attachment rail 20, they still provide a significant improvement over the stationary attachment of the prior art.

While the attachment member 128 can be used to selectively attach the belt 136 to various positions along the attachment rail 120, it can also be used to secure the belt to a single location. In such a situation, however, the attachment rail 120 would be made slidable or otherwise movable relative to the platform 116. If the attachment rail 120 is ruled, i.e. provided with markings indicating distance, the therapist need only slide the attachment rail 120 relative to the platform 116 so that the attachment member 128 is disposed a predetermined distance from a point on the platform.

Figure 12:
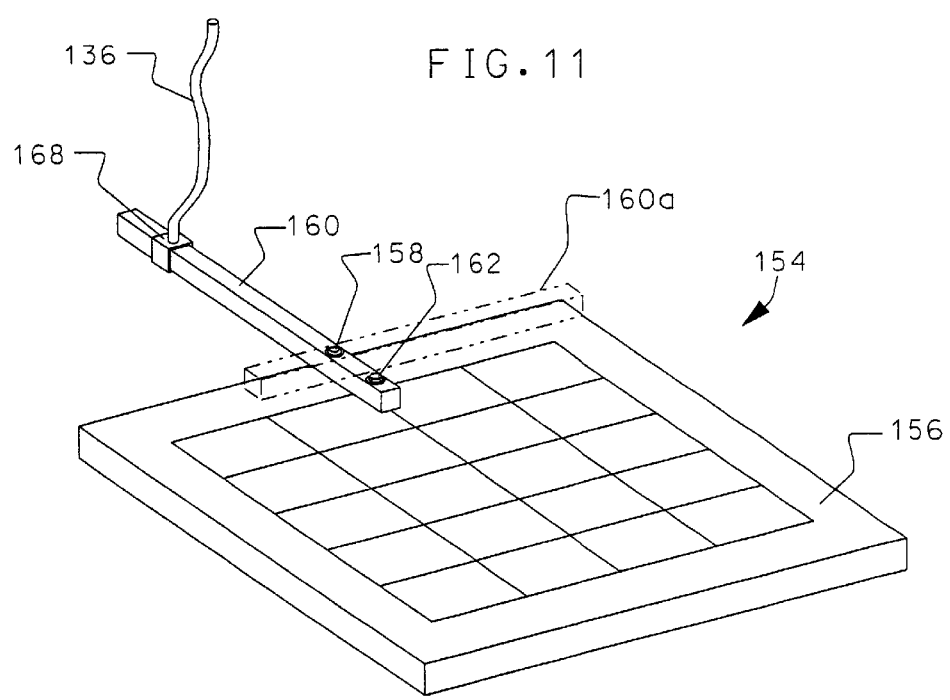
FIG. 12 shows a top perspective views of yet another embodiment of a mobile lift system in accordance with the principles of the present invention.

Turning now to FIG. 12, there is shown yet another embodiment of a mobile lift system 154 formed in accordance with the principles of the present invention. The mobile lift system 154 includes a platform 156 and an attachment rail 160. Unlike the prior two configurations in which the attachment rail (20 or 120) can be removed from the platform (16 or 116), the attachment rail 160 is configured to be substantially permanently attached to the platform 156. Thus, the attachment rail 160 is attached to the platform 156 by an attachment means such as a rivet 158, bolt, or other fastener.

While the attachment rail 160 is not meant to be removed from the platform 156 for transport and storage, it is attached to the platform 156 in such a manner that the attachment rail is able to pivot with respect to the platform when not in use. For example a bolt 162 may be used to engage a threaded opening in the platform 156 to secure the attachment rail 160 against pivoting while the patient is pulling upwardly on the belt 176 and attachment member 168.

When the mobile lift system is not in use, the bolt 162 can be removed. The attachment rail 160 can then be aligned with the platform 156 to minimize the overall dimensions of the mobile lift system 114 during transport and storage as shown by dashed line 160a. When the mobile lift system 154 is needed again, the attachment rail 160 need merely be pivoted back into place and the bolt 162 advanced until it securely engages the platform. Of course, dowels, or other movable stops could be used in place of the bolt 162 to hold the attachment rail in alignment during use.

Thus, there is disclosed an improved mobile lift system. Those skilled in the art will appreciate numerous modifications which could be made without departing from the spirit of the invention. The appended claims are intended to cover such modifications.

What is claimed is:

1. A mobile lift system comprising:
   a platform configured for having a patient stand thereon;
   an attachment rail configured for attachment to the platform and extending therefrom; and
   a belt attachment member selectively placeable along the attachment rail at predetermined distances from the platform.

2. The mobile lift system according to claim 1, further comprising a belt.

3. The mobile lift system according to claim 1, wherein the platform has a grid formed thereon.

4. The mobile lift system according to claim 1, wherein the attachment rail is selectively attachable to and removable from the platform.

5. The mobile lift system according to claim 1, further comprising means for attaching the attachment rail to the platform.

6. The mobile lift system according to claim 5, wherein the means for attaching comprises a fastener about which the attachment rail can pivot.

7. The mobile lift system according to claim 6, wherein the attachment rail is pivotable between a first position in which the attachment rail extends from the platform, and a second position in which the attachment rail is aligned along the platform.

8. The mobile lift system according to claim 5, wherein the means for attaching the attachment rail to the platform comprises a pin which engages the platform.

9. The mobile lift system according to claim 8, wherein the means for attaching the attachment rail to the platform further comprises a bracket attached to the attachment rail, and configured for receiving the pin therethrough.

10. The mobile lift system according to claim 5, wherein the means for attaching the attachment rail to the platform comprises an attachment post and an attachment post notch.

11. The mobile lift system according to claim 1, wherein the attachment rail has markings disposed thereon for determining location.

12. The mobile lift system according to claim 1, wherein the belt attachment member comprises a mechanism for selectively holding the belt attachment member at a set location along the attachment rail.

13. The mobile lift system according to claim 12, wherein the belt attachment member comprises a lever.

14. The mobile lift system according to claim 12, wherein the belt attachment member comprises a sleeve.

15. The mobile lift system according to claim 12, wherein the belt attachment member comprises a pin.

16. The mobile lift system according to claim 15, wherein the attachment rail comprises a plurality of holes.

17. The mobile lift system according to claim 1, wherein the attachment rail is slidable relative to the platform.

18. The mobile lift system according to claim 1, wherein the system further comprises at least one bracing member attached to the attachment rail.

19. The mobile lift system according to claim 18, wherein the bracing member is provided with a compressible material for engaging a flooring surface.

20. A mobile lift system comprising:

a platform configured for standing on by a user;

an attachment rail selectively attachable to the platform such that the attachment rail extends from the platform a predetermined distance;

an attachment member movable along the attachment rail to a number of predetermined locations; and a belt attached to the attachment member.

21. The mobile lift system according to claim 20, wherein the platform has a notch and wherein the attachment rail has an attachment post which nests in the notch to secure the attachment rail to the platform.

22. The mobile lift system according to claim 20, wherein the platform has a receptacle, wherein the attachment rail has a bracket, and further comprising a pin for passing through the bracket and into the receptacle to secure the attachment rail to the platform.

23. The mobile lift system according to claim 20, wherein the attachment rail further comprises at least one bracing member.

24. A method for forming a mobile lift system, the method comprising:

selecting a platform;

positioning an attachment rail and an attachment member so that the attachment rail extends from the platform and so that the attachment member is movable to a number of locations along the attachment rail at varying distances from the platform.

25. The method according to claim 24, wherein the method comprises attaching the attachment rail to the platform.

26. The method according to claim 24, wherein the method comprises rotating the attachment rail relative to the platform.

27. The method according to claim 24, wherein the method comprises using an attachment rail having a plurality of marking disposed thereon for determining location of the attachment member.

28. A method for testing a patient comprising:

disposing the patient on a mobile lift system having a platform, an attachment rail extending from the platform, and an attachment member attached to a belt, the attachment member being movable to various locations along the attachment rail;

having the patient pull upwardly to cause the belt to pull upwardly against the attachment member when the attachment member is disposed at a first location;

moving the attachment member to a second location; and having the patient pull upwardly to cause the belt to pull upwardly against the attachment member.

29. The method according to claim 28, wherein the method comprises recording the location of the attachment member and the force with which the patient pulled upwardly at that location.

30. The method according to claim 28, wherein the method further comprises moving the attachment member to a third location and having the patient pull upwardly to cause the belt to pull upwardly against the attachment member.

31. The method according to claim 30, wherein the method comprises recording the position of the third location and the force exerted by the patient.

32. The method according to claim 28, wherein the method further comprises maintaining the patient's feet at a predetermined location on the platform.

33. The method according to claim 28, wherein the method further comprises detaching the attachment rail from the platform after testing of the patient is complete.

34. The method according to claim 28, wherein the method further comprises selecting an attachment rail having a bracing member disposed thereon for preventing lifting of the platform by mechanical leverage when the patient leans backward.

* * * * *